United States Patent [19]
Hetrick et al.

[11] Patent Number: 5,275,712
[45] Date of Patent: Jan. 4, 1994

[54] WIDE RANGE WORKFUNCTION BASED A/F SENSOR

[75] Inventors: Robert E. Hetrick, Dearborn Heights; Allen L. Schamp, Dearborn, both of Mich.

[73] Assignee: Ford Motor Company, Dearborn, Mich.

[21] Appl. No.: 913,311

[22] Filed: Jul. 14, 1992

[51] Int. Cl.$^5$ ............................................. G01N 27/26
[52] U.S. Cl. ................................... 204/425; 204/426; 204/427; 324/470
[58] Field of Search ............... 204/406, 412, 425, 426, 204/427, 153.18; 324/470, 33

[56] References Cited

U.S. PATENT DOCUMENTS

| | | | |
|---|---|---|---|
| 3,416,070 | 12/1968 | McGowan, Jr. | 324/33 |
| 4,272,329 | 6/1981 | Hetrick | 204/153.18 |
| 5,028,544 | 7/1991 | Rasulev et al. | 324/470 |

OTHER PUBLICATIONS

SAE Paper No. 860409 "Wide-Range Air-Fuel Ratio Sensor" (no date available).

*Primary Examiner*—T. Tung
*Assistant Examiner*—Bruce F. Bell
*Attorney, Agent, or Firm*—Peter Abolins; Roger L. May

[57] ABSTRACT

A sensor determines a wide range of air-to-fuel ratio values (A/F) about the stoichiometric A/F in a gaseous mixture which has oxidizing and reducing species as might be found in an automotive exhaust. The sensor includes a surface that serves simultaneously as the working electrode of a solid-state oxygen concentration cell and as a surface whose workfunction changes from a higher to a lower value as the oxidizing and reducing species in the adjacent gas phase, and in interaction with the surface, pass from an excess oxidizing to the excess reducing condition about the stoichiometric ratio. In one embodiment, the surface exposed to the gas in question is the emitter electrode of a thermionic diode which emits positively charged alkali ions into the exhaust ambient where they are collected by a nearby collector electrode. Changes in the ratio of the oxidizing and reducing species about the stoichiometric ratio produce corresponding changes in the thermionic emission. Oxygen pumping to or from the working electrode modifies the thermionic emission in a systematic way to provide a pumping method of operation in which the magnitude of the pump current required to maintain the thermionic emission current at some preset value despite changes in the A/F ratio of the ambient leads to a relationship between pump current and A/F that can be used to sense the A/F.

7 Claims, 4 Drawing Sheets

FIG.8B $$V_R \sim \frac{I(L) - I(R)}{2}$$

WIDE RANGE WORKFUNCTION BASED A/F SENSOR

BACKGROUND OF THE INVENTION

1. Field of the Invention

This invention relates to an electrical means to measure over a wide range the ratio of the concentrations of oxygen and other oxidizing gaseous species to the concentrations of the various reducing gaseous species such as hydrocarbons, hydrogen and carbon monoxide as might be found in the automotive exhaust.

2. Prior Art

Under many operating conditions, it is desirable to keep the A/F (the ratio of the mass of air to the mass of fuel) at the input to the cylinders of an internal combustion engine near the so called stoichiometric value. At this value harmful exhaust emissions are minimized (and thus most easily reduced further by an exhaust gas catalyst), because there is just enough oxygen present to react with all of the injected hydrocarbons.

To maintain a tight tolerance on A/F control over the life of the car, widespread use has been made of feedback control methods using the so called exhaust gas A/F sensors as the feedback element. These high temperature, solid state devices detect various aspects of the ratio of the concentrations of oxidizing species (mostly oxygen) and reducing species (a mixture of hydrocarbons, hydrogen and carbon monoxide) in the automotive exhaust. Under steady state conditions these aspects are in turn proportional to comparable aspects of the A/F at the input to the cylinders.

Stoichiometric A/F sensors have a step-like transfer function in which a high/low output is obtained when the ambient gas is, for example, rich/lean of stoichiometry. A very sharp transition between the extreme outputs occurs in a narrow A/F region around stoichiometry. Variations in the output in the regions rich or lean of stoichiometry are generally quite small. One consequence of this type of transfer function is that feedback is accomplished in a limit cycle or oscillatory manner. Thus the A/F oscillates with a period on the order of a second about the stoichiometric A/F. These sensors are fabricated from oxide materials and typically employ either an electrochemical or resistive mechanism. For example, the oxygen ion conducting $ZrO_2$ doped with $Y_2O_3$ is the solid electrolyte used in combination with catalytically active Pt electrodes in most electrochemical devices. Porous $TiO_2$ dosed with fine grains of Pt particles is frequently used for the resistive devices.

In appropriate circumstances it is desirable to operate rich (excess fuel) or lean (excess air) of the stoichiometric A/F. Thus rich conditions may be required for "cold start" and high "load." Lean conditions favor fuel economy. To obtain the advantages of feedback control under various circumstances, it is desirable to have a wide-range A/F sensor. There are known a variety of electrochemical structures made from the $ZrO_2$ material mentioned above which combine the processes of oxygen pumping and emf measurements using the oxide cells to obtain a wide range of A/F measurements both rich and lean of stoichiometry with a near linear transfer function. See, for example, those described in U.S. Pat. No. 4,272,329 to Hetrick or a publication by Ueno et al. in "Wide-Range Air-Fuel Ratio Sensor" in SAE Paper No. 860409.

SUMMARY OF THE INVENTION

This invention includes a device structure and a method of operation which accomplishes wide-range A/F measurement in a gaseous ambient containing oxygen and reducing species. The method combines the processes of oxygen pumping with oxide electrochemical cells with that of measuring the change in the workfunction of an appropriate surface (which is simultaneously the working electrode, as opposed to the reference electrode, of the electrochemical cell). The chemical species in the gas phase immediately adjacent to the surface, and importantly in chemical interaction with the surface, make a change from net oxidizing to net reducing conditions as a result of the combined processes of oxygen pumping and changes in the gas phase at large. One method by which the workfunction changes are measured is based on the thermionic emission of positively charged alkali metal ions from the surface, which is simultaneously the surface of the working electrode that is exposed the gas phase, into the exhaust gas. A nearby collector electrode subsequently collects these ions.

Alkali metals are common impurities (as well as deliberate dopants) in many metals including platinum (Pt). Platinum is often used as the electrode material (frequently in a porous form) of gas-sensing solid electrolyte cells. Further, the alkalis (e.g. Li, Na, K, Cs) are common impurities or constituents of the ceramic material underlying the Pt electrodes. At the moderately elevated temperatures ($>400°$ C.) at which the ceramic A/F sensors operate, these alkalis can be thermionically emitted as positive ions which can then be collected by a nearby electrode and the emission current measured.

This thermionic current (typically in the nA regime) is found in the case of Pt (as well as other metals) to be exponentially sensitive to the workfunction of the emitting surface. In the case of some materials like Pt, the workfunction can change substantially due to the adsorption of gas phase species (e.g. the workfunction of Pt can increase by 0.7 V) due to the adsorption of oxygen). Further, when the material is exposed to a mixture of gases which will react catalytically through an adsorption mechanism, the workfunction may change significantly and reversibly on passage through the stoichiometric ratio of such a reactive gas mixture thus effecting a significant change in the thermionic current. The current is high under oxygen excess or lean conditions corresponding to the large workfunction and low under oxygen deficit or rich conditions corresponding to a low workfunction. This serves to sense or mark that ratio.

If the Pt, or material with similar properties which is exposed to an atmosphere containing oxidizing and reducing species, is simultaneously an electrode of an oxygen concentration cell (as for example one made from the oxide $ZrO_2$ doped with the oxide $Y_2O_3$), then oxygen can be electrochemically pumped to or from the electrode surface by passing current in the appropriate direction through the cell. It has been found that as a result of this pumping, the workfunction of the Pt electrodes can be changed. In an oxidizing ambient, pumping oxygen away from the exposed electrode can reduce the workfunction, while pumping oxygen to a Pt surface exposed to a reducing gas can increase the workfunction.

Thus one can adopt a method in which one pumps oxygen to or from the surface in question in just the right amount to keep the thermionic current midway between its lean (high current) and rich (small current) values. The more one is lean (rich) of stoichiometry the more oxygen one must pump away from (toward) the surface to achieve the intermediate value of the emission current. In this way the magnitude and direction of the electrochemical pumping current required to maintain the thermionic emission current at a preset value intermediate between its rich and lean extremes becomes a measure of the A/F.

BRIEF DESCRIPTION OF THE DRAWINGS

FIG. 8b shows the schematic diagram of the negative feedback circuit which could be used to implement the measurement method leading to the characteristic shown in FIG. 7a.

DETAILED DESCRIPTION OF THE INVENTION

Alkali metals such a Li, Na, K, and Cs are common impurities or deliberate additives in many ceramic and metal materials. When these solids are heated to a modest temperature, the volatile alkalis can be thermally evaporated from the host solid. Since the ionization potential, IP, of many of the alkalis is low, the alkalis can be emitted as positive ions as well as neutral atoms. Thermionic emission tends to occur when the IP of the alkali is small or comparable to the workfunction of the host. Thus Cs with an IP of approximately 3.9 V is usually emitted as an ion from host metals such as Pt or Au which have a workfunction of about 5 V. On the other hand Li with an IP of about 5.8 V is usually emitted as an atom. This trend is reasonable from an energetic viewpoint since one can imagine that a large workfunction for the host allows for the ready transfer of the outermost electron of a low IP alkali to the host with subsequent thermal emission of an alkali ion at elevated temperature.

Figure 1:
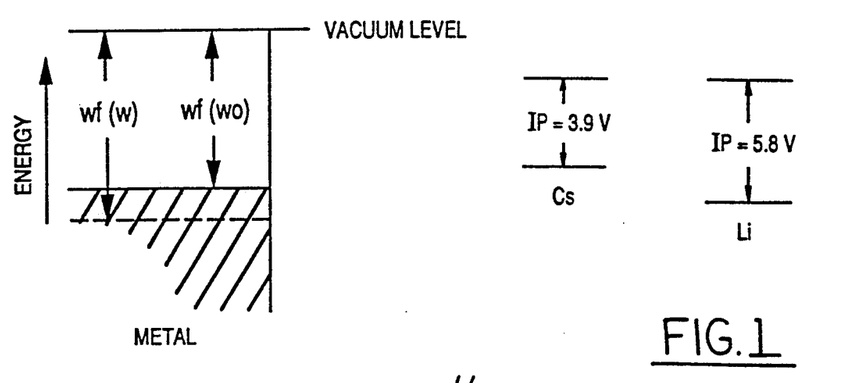
FIG. 1 is a schematic diagram showing the workfunction, wf, of the thermionically emitting surface with, wf(w), and without, wf(wo), an oxide layer as well as the ionization potential, IP, (these values are appropriate for alkali atoms in the gas phase and may be modified somewhat as the alkali atoms approach a surface) of two alkali metal atoms which may be absorbed on the surface and thus thermionically emitted if the temperature is raised.

These ideas are illustrated schematicaly in FIG. 1 which shows the material workfunction with, wf(w), and without, wf(wo), an oxide layer. This parameter is proportional to the energy required to remove the most energetic electron that is bound in the solid to the vacuum energy level where it could leave the solid if drawn away with an electric field for example. The energy scale is vertical in the drawing. IP is the comparable parameter for atoms of molecules and the values for two alkali metals (which have low values of IP) are shown. Electrons may transfer between atoms or molecules hitting the surface and the solid. Electrons would move from the species with the lowest binding energy to that with the greatest binding energy.

As will be discussed further below, when the solid is exposed to an oxidizing gaseous ambient, the oxidizing species can interact with the surface and modify the workfunction (e.g. to a new value, wf(w), assuming that oxygen is the oxidizing species) thereby changing the rate of the thermionic emission. For electrons a high emission rate is promoted by a low workfunction. However, for positive ion emission as in the present case, the situation is more complicated and usually a high workfunction promotes stronger emission since it becomes easier for the surface impurity species (the alkali atom) to leave its outermost electron in the solid and thermionically emit as an ion rather than thermally evaporate as an atom. Solid state ion emitters based on this principle are well known and are attractive in some applications since one avoids the complexity and cost of generating a gaseous plasma as an ion source.

Figure 2:
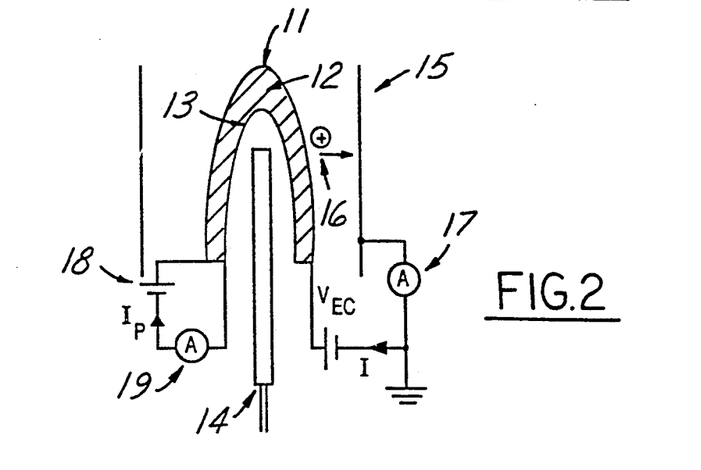
FIG. 2 shows a schematic diagram of a wide-range A/F sensor in which alkali ions are thermionically emitted from a metal surface (to a concentric collector electrode) which is simultaneously one of the electrodes of a solid-state oxygen concentration cell. The electrochemical pumping of oxygen to or from the emitting surface, as represented by the current $I_p$, systematically affects the magnitude of the thermionic emission in a manner which allows for a wide-range A/F sensor.

FIG. 2 shows a schematic diagram of a wide-range A/F sensing device which employs the thermionic alkali ion emission mechanism. The emitting surface 11 is a porous layer (e.g. 5 microns thick) of Pt. Emitting surface 11 is the outer electrode of an oxygen concentration cell composed of oxygen ion conducting ceramic $ZrO_2$ doped with a substantial amount of $Y_2O_3$ (a few atomic percent) 12 to generate the oxygen ion vacancies which allows for oxygen conduction. The inner electrode 13 is also porous Pt. The alkali metal could be incorporated as a dopant in both the Pt and the underlying ceramic. In the latter case diffusion of alkali atoms to the Pt. surface from the underlying ceramic would ensure an extended operation for the device.

In an automotive application the device would be inserted into the exhaust system at some point so that the outer electrode would be exposed to the exhaust while the inner electrode would be exposed to outside air. Other means for generating the reference atmosphere without using outside air as a reference would be possible in a more complex structure. The ceramic element might take the form of a tube closed at one end, and a pencil-like ceramic heating element 14 inserted into the open end could be used to elevate the temperature of the entire structure to a desired temperature of operation in excess of approximately 450° C. For the particular materials discussed above, this or higher temperatures would allow for both oxygen-ion conduction in the ceramic and thermionic emission from the Pt.

In this particular geometry a collector electrode 15 in the form of a hollow cylinder concentric with the emitting structure is positioned to collect the emitted ions 16 when emitting surface 11 is biased positively with respect to collector electrode 15 ($V_{EC}$ is positive). An ammeter 17 is also placed in the emitter-collector circuit to measure the magnitude of the emission. Similarly a power supply 18 and current measuring device 19 are required in the oxygen pumping circuit to activate and monitor the rate of the pumping process. The cylindrical geometry of the structure is not essential to its operation.

Figure 3A:
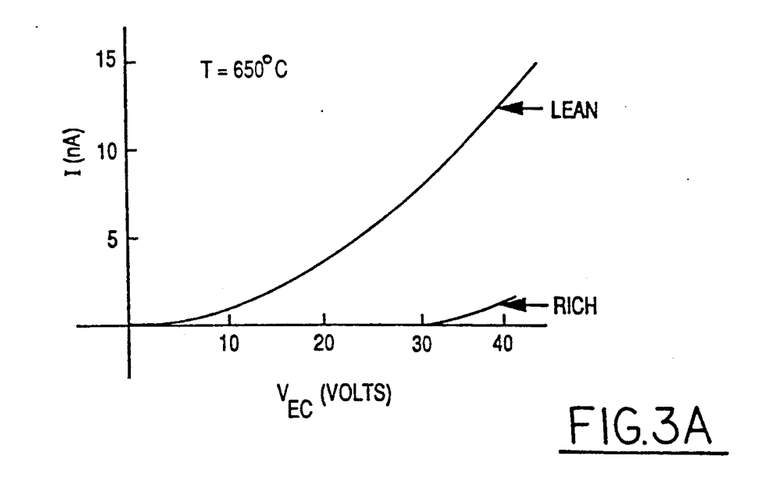
FIG. 3a is a graphical representation of the thermionic current I as a function of the emitter to collector voltage ($V_{EC}$) for rich and lean ambient gas conditions.

FIG. 3a shows a typical plot of I versus $V_{EC}$. When emitter 11 is negative with respect to collector 15, the current flow is very low (in the subpicoampere regime). Current flow with the opposite emitter bias shows a greater than linear increase in magnitude with bias. Typical current magnitudes are at the nA level with current levels increasing with temperature and emitter surface area. In summary, the current voltage characteristic is that of a thermionic diode in which the emitter species is of a positive sign and the conducting medium is quite resistive compared to a vacuum. In this case the resistance is provided by the collisions of the positive ions with the neutral molecules of the ambient gas phase (e.g. air) which results in an ion mobility on the order of 3 $cm^2$/volt-sec at 100 kPa. Numerous results confirm this basic model.

Figure 3B:
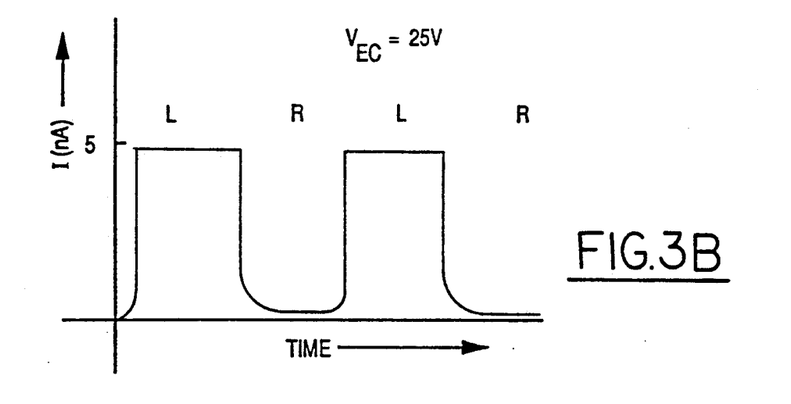
FIG. 3b is a graphical representation illustrating the variation in I with time as the ambient is alternately switched between rich and lean conditions.

FIG. 3a also shows the important result that exposure of emitting surface 11 to a rich ambient causes a large reduction (as large as a factor of 100 depending on the temperature) in the emission at all collector-emitter voltages. The change from large to small currents occurs at the stoichiometric ratio of the oxidizing and reducing gases in the ambient. FIG. 3b further illustrates this latter point by showing that the current switches in time between its high and low values as the stoichiometry of the ambient gas is varied from lean to rich conditions. Mixtures of propane and oxygen diluted in nitrogen were used to establish a desired gas ratio. The emission current is not constant for all lean or rich mixtures, but the changes are small, except for those occurring at stoichiometry, when the reactive gases are a small fraction of the total ambient atmosphere. The likely mechanism causing the change in I is the gas induced change in emitter workfunction with variation in the stoichiometry of the gas phase.

As discussed above, the workfunction is a key factor in determining whether alkali metals are thermally emitted as ions or atoms. Similarly, the rate of emission (or the ion current) at a given temperature has been shown in some cases to vary with the workfunction. Thus, the thermionic emission from a high workfunction host is greater than from a low workfunction host. In the case of Pt, it is well known that a surface exposed to oxygen will adsorb that oxygen in a way which increases the workfunction. When the ambient is modified so that the concentration of reducing species are in excess of the stoichiometric amount, these species will react with and thus remove that adsorbed oxygen. The effect of reducing the workfunction, and correspondingly the rate of thermionic emission, attends this process.

Figure 4:
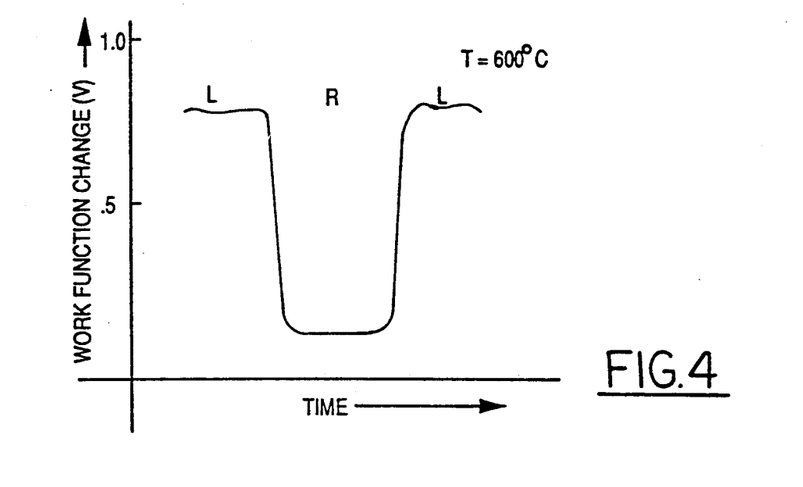
FIG. 4 is a graphical representation of the variation in the workfunction of a Pt emitter electrode as the ambient gas is varied between lean and rich conditions.

FIG. 4 shows a plot of the change in the Pt electrode workfunction versus time as the ambient gas at 600° C. is varied from lean to rich and back to lean conditions. The workfunction change was found to decrease by as much as 0.7 V at stoichiometry as the ambient was varied from lean to rich conditions. Note that only changes in and not the absolute value of the workfunction are obtained by this method. The effect which enables the wide-range A/F sensor is the observation that oxygen pumping also affects the workfunction of the Pt electrodes just as a change in exhaust gas conditions does.

Figure 5:
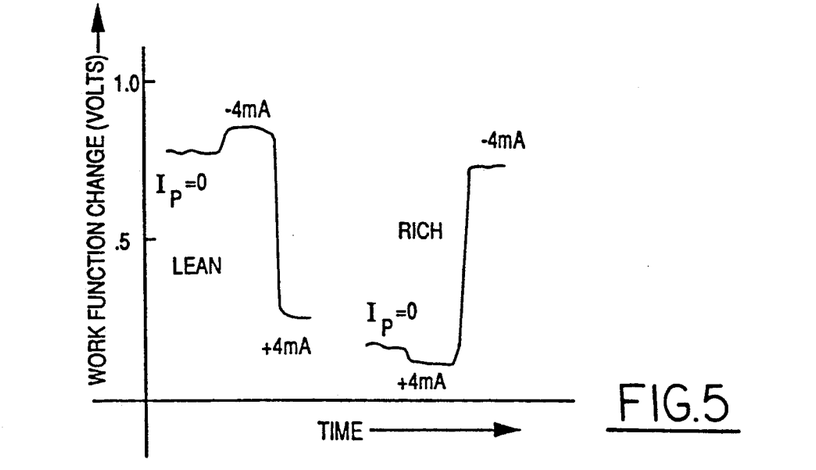
FIG. 5 is a graphical representation of the variation in a Pt emitter workfunction due to the electrochemical pumping of oxygen under both lean and rich ambient conditions.

This phenomena is illustrated in FIG. 5 where oxygen pumping as measured by $I_P$ is shown to modify the workfunction of the outer electrode of the oxygen concentration cell of FIG. 2. In particular, it is found that the workfunction is always increased when current is pumped to that electrode and decreased when oxygen is pumped in the opposite direction. FIG. 5 shows that this result holds whether one is rich or lean or stoichiometry. Qualitatively the greatest effect (in V-$cm^2$/amp, the change in workfunction per unit current density) occurs in the vicinity of stoichiometry when oxygen is pumped from the working (or emitting) electrode under lean conditions or to the working electrode under rich conditions. The magnitude of this effect however depends strongly on the A/F. Thus if one is very lean, the passage of large amounts of pumping current (in either direction) under conditions where the voltage drop across the cell is largely Ohmic, results in virtually no change in workfunction.

In summary, the largest pumping effects occur for circumstances in which the working electrode is largely depleted of oxygen. Under these conditions, a part of the voltage applied to the cell (the other part being the Ohmic potential drop) will fall between the depleted working electrode and the adjacent reference electrolyte as "over potential" to promote the electrochemical reaction at the working electrode. Phenomena occurring on the working electrode as a result of the over potential are presumably responsible for the change in workfunction.

Figure 6:
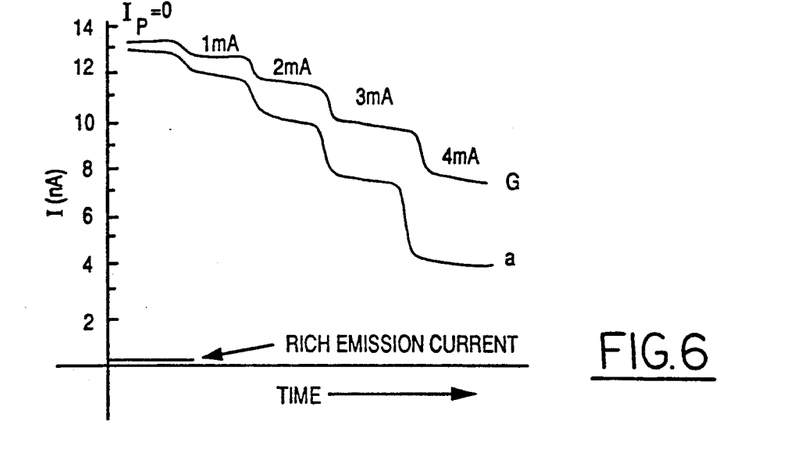
FIG. 6 is a graphical representation of the change in I versus time under two lean A/F conditions (both close to stoichiometry) as oxygen is electrochemically pumped away from the emitting surface at increasing rates as measured by the pump current $I_p$. The largest changes occur when the A/F is closest to stoichiometry. Propane and oxygen diluted in nitrogen at a total pressure of 100 kPa were used as the reducing and oxidizing gases respectively.
Figure 7:
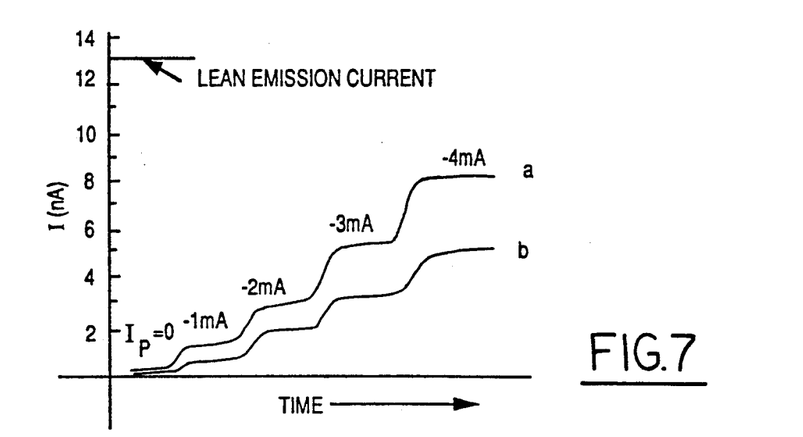
FIG. 7 is a graphical representation of the change in I versus time under two rich A/F conditions (both conditions close to stoichiometry) as oxygen is pumped toward the ion emitting surface at increasing rates as measured by $I_p$. The largest changes occur when the A/F is the closest to stoichiometry.

The use of oxygen pumping to implement a wide range A/F sensor is possible because the pumping current produces changes in the thermionic current (as a result of corresponding changes in the workfunction) that are consistent with those changes in the thermionic current resulting from variations in the gas phase. In particular, pumping oxygen from the working electrode under lean conditions reduces I while pumping oxygen to the working electrode under rich conditions increases I. This effect is illustrated in FIGS. 6 and 7. In FIG. 6, curve "a" shows that oxygen pumped from the working electrode under lean conditions causes I to decline. The amount of decline increases monotonically with $I_P$. If one is leaner as is the case for curve "b", then the same value of $I_P$ does not reduce I by the same amount. Put differently, a larger $I_P$ would be required to bring I to the same reduced value for a leaner A/F.

Figure 8A:
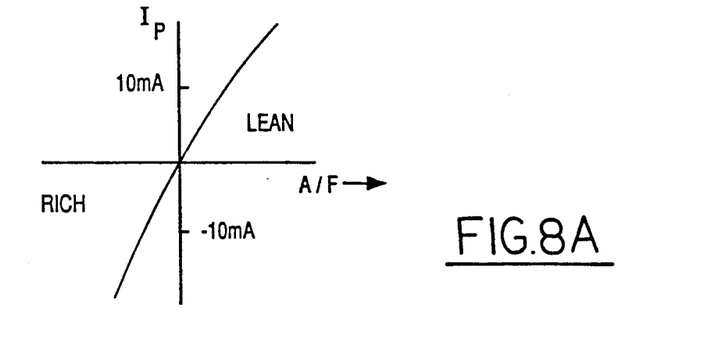
FIG. 8a is a graphical representation of the transfer characteristic for an extended range A/F sensor based on the effect of oxygen pumping, as measured by $I_p$, on the thermionic emission. To realize this characteristic, oxygen is pumped to (in the rich region) or from (in the lean region) the emitting electrode to maintain the thermionic current midway between its rich and lean values as the A/F is varied.

A completely analogous situation is shown in FIG. 7. Pumping from the reference to the working electrode under rich conditions causes I to increase with the larger increase for a given $I_P$ occurring when one is closer to stoichiometry. These results indicate that if one were to pump oxygen toward or away from the working electrode as required to maintain I at a value intermediate between its rich and lean extremes, one would achieve a device with a transfer characteristic as shown FIG. 8a where the required $I_P$ would be a monotonic function of A/F for a given application (i.e. the same type of fuel or reducing species).

Figure 8B:
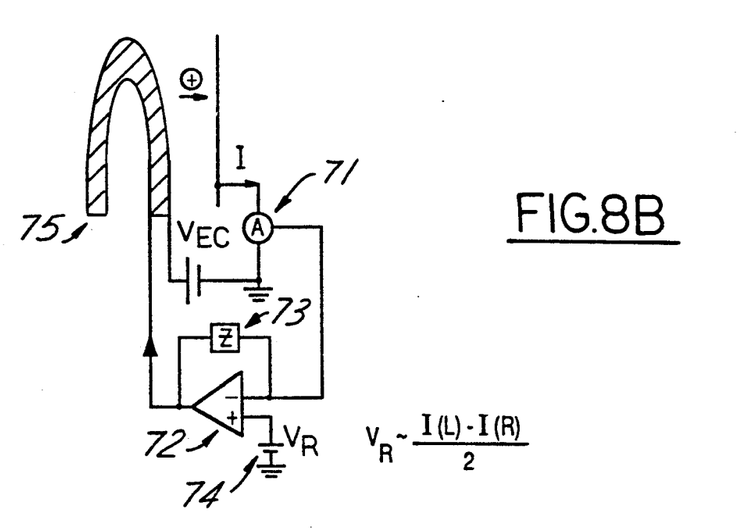

This method can be implemented with the negative feedback circuit shown in FIG. 8b where the output of the current sensor 71 (with a voltage output proportional to the thermionic current) in the collector circuit is applied to the negative input of an operational amplifier 72 whose feedback impedance 73 is represented by Z. An emf $V_R$, 74 whose value is intermediate between that corresponding to the large lean current and the small rich current is applied to the other (positive) input. The output of the amplifier is applied to the electrochemical cell 75. The action of this circuit is that the amplifier will put out sufficient $I_P$ of the correct sign that through the effect illustrated in FIGS. 5 and 6, the workfunction of the emitter will be maintained at a value which will produce an I that corresponds to $V_R$ (through the transfer characteristic of the ammeter) despite changes in the gas phase. The required value of $I_P$ to accomplish this will be proportional to the ratio of oxidizing to reducing species concentrations.

Various modifications and variations will no doubt occur to those skilled in the various arts to which this invention pertains. For example, the geometric configuration of the sensor structure need not be cylindrical but might advantageously have a planar geometry. These and all other variations which basically rely on the teachings through which this disclosure has advanced the state of the art are properly considered within the scope of this invention.

What is claimed:

1. A structure for sensing the ratio of the concentrations of an oxidizing to a reducing gaseous species over a wide range about their stoichiometric ratio in an ambient gas phase by combining means for oxygen pumping using a solid electrochemical cell with a subsidiary device structure for measuring a reversible change in the workfunction of a material located in said subsidiary structure, the surface of which material is exposed to and in chemical interaction with the gaseous species in question, and in particular the workfunction value changes from a high (low) to a low (high) value at the point where the ratio of the concentrations of the oxidizing and reducing species passes through its stoichiometric value beginning with oxidizing (reducing) and ending with reducing (oxidizing) conditions respectively, the material simultaneously serving as a working electrode of the electrochemical cell wherein:

said solid electrochemical cell incorporates a solid electrolyte for conducting ionized oxygen species and shaped to establish a partition of the electrolyte material so that different gaseous atmospheres can be maintained on either side of the partition, and such that electrodes can also be affixed on the opposing sides of the partition which are physically porous and electrochemically pump oxygen from a gas phase adjacent to one electrode and to the gas phase adjacent to the other electrode when an emf is applied between the two opposing electrodes;

said opposing electrodes including a reference electrode exposed to a reference atmosphere of known oxygen concentration, and said working electrode exposed to the gas whose properties are to be sensed;

said reference atmosphere contains a sufficient concentration of a form of oxygen to allow for the conduction of oxygen through said electrolyte to the atmosphere next to said working electrode at a high enough rate to effect a change in the workfunction of said working electrode;

said working electrode has the property that when oxygen is pumped from the atmosphere next to said working electrode to said reference atmosphere under conditions such that the ratio of the oxidizing to reducing species in the adjacent gas phase is larger than its stoichiometric ratio, then the workfunction of said working electrode is reduced, and when oxygen is pumped to said working electrode under conditions such that the ratio of the oxidizing to reducing species in the adjacent gas phase is less than its stoichiometric ratio then the workfunction of said working electrode is increased;

said working electrode is such that when the oxidizing species are in excess of their stoichiometric amount with respect to the reducing species then the oxidizing species in interaction with the surface of said working electrode cause the workfunction to increase to a larger value than that workfunction value occurring when the reducing species, also in interaction with the surface of said working electrode, are in excess of their stoichiometric amount with respect to the oxidizing species;

said subsidiary device for measuring the workfunction of said working electrode includes a first electrical circuit means whose output is proportional to the change in the magnitude of the workfunction; and a second circuit means coupled to said electrochemical cell includes a source of emf to cause oxygen pumping through said cell and whose output is a function of the output of the first circuit means.

2. A structure for sensing the ratio of the concentrations of an oxidizing to a reducing gaseous species over a wide range about their stoichiometric ratio as recited in claim 1 wherein:

said second circuit means includes the negative input, of a negative feedback circuit, to which is coupled the electrical output of said first electrical circuit which acts as the workfunction measuring device, and an output coupled to said electrochemical cell wherein that an electrochemical current of oxygen is pumped between said opposing electrodes of said electrochemical cell at a rate and in a direction such that the workfunction as measured by said first circuit means can be maintained at a constant value that is intermediate between that observed when the oxidizing species are in excess of the reducing species with respect to their stoichiometric ratio and that observed when the reducing species are in excess of the oxidizing species with respect to their stoichiometric amounts, with the result that the oxygen pumping current is proportional to the ratio of the concentrations of the oxidizing to reducing species.

3. A structure as recited in claim 2 wherein:
said working electrode material is platinum;
said electrolyte is zirconium oxide doped with sufficient yttrium oxide to allow for oxygen ion conductivity; and
said electrolyte has a general cylindrical shape closed at one end, with said working electrode on an exposed surface and said reference electrode on an interior surface.

4. A structure as recited in claim 2 in which at least one of said working electrode and said electrolyte are doped with atomic species whose ionization potential is small with respect to the workfunction of the working electrode, and whose binding to the working electrode depends on the material of the working electrode, at the working temperature of the device these species will be thermionically emitted from said working electrode surface as positive ions into the surrounding gaseous ambient;
  said working electrode having an emitting surface, said supporting electrolyte and said dopant species being ones in which the rate of thermionic emission of the dopant is reversibly increased or decreased with an increase or decrease in the workfunction of said emitting surface;
  a collector electrode electrically insulated and spaced from said emitting surface so that the gas phase can establish itself between said collector electrode and said emitting surface, and emitted ions can be electrically collected at said collector electrode;
  said first circuit means coupled to said emitting surface and said collector electrode to provide a potential difference between said collector electrode and said emitting surface to cause ion collection and containing a current sensing means which has an electrical output proportional to the magnitude of the collected thermionic current; and
  a heating element associated with said working electrode with said emitting surface in order to raise the electrode temperature to a high enough value to allow thermionic emission.

5. A structure for sensing the ratio of the concentrations of an oxidizing to a reducing gaseous species over a wide range about their stoichiometric ratio wherein:
  said second circuit means includes the negative feedback and an input coupled to an electrical output of said first electrical circuit which acts as the workfunction measuring device, and an output coupled to said electrochemical cell wherein an electrochemical current of oxygen is pumped between said opposing electrodes of said electrochemical cell at a rate and in a direction such that the workfunction as measured by said first circuit means can be maintained at a constant value that is intermediate between that observed when the oxidizing species are in excess of the reducing species with respect to their stoichiometric ratio and that observed when the reducing species are in excess of the oxidizing species with respect to their stoichiometric amounts, with the result that the oxygen pumping current is proportional to the ratio of the concentrations of the oxidizing to reducing species; and at least one of said working electrode and said electrolyte are doped with species to serve as a reservoir of chemical species which is thermionically emitted from said working electrode surface as positive ions into the surrounding gaseous ambient;
  said working electrode having an emitting surface, said supporting electrolyte and said dopant species being ones in which the rate of thermionic emission of the dopant is reversibly increased or decreased with an increase or decrease in the workfunction of said emitting surface;
  a collector electrode is electrically insulated and spaced from said emitting surface so that the gas phase can establishes itself between said collector electrode and said emitting surface, and emitted ions can be electrically collected at said collector electrode;
  said first circuit means coupled to said emitting surface and said collector electrode to provide a potential difference between said collector electrode and said emitting surface to cause ion collection and containing a current sensing means which has an electrical output proportional to the magnitude of the collected thermionic current;
  a heating element is associated with said working electrode with said emitting surface in order to raise the electrode temperature to a high enough value to allow thermionic emission, and
  said dopant species is an alkali metal.

6. A combined electrochemical and thermionic structure for sensing the ratio of the concentrations of an oxidizing to a reducing species in an ambient gas phase over a wide range about a stoichiometric ratio of the oxidizing and reducing species including:
  a solid electrochemical cell including a solid electrolyte positioned between two opposing electrodes, one opposing reference electrode being exposed to a reference atmosphere and the other opposing working electrode being exposed to the gas whose properties are to be sensed;
  said cell having said electrolyte for conducting negatively charged oxygen ions and said electrodes being physically porous and electrochemically pump oxygen from a gas phase adjacent to one of said opposing electrodes to the gas phase adjacent to the other of said opposing electrodes;
  said reference atmosphere containing enough of a form of oxygen to allow for the conduction of oxygen to said working electrode at a high enough rate to effect a thermionic emission processes that is occurring simultaneously at said working electrode;
  said working electrode having the property that when oxygen is pumped from said working electrode under conditions such that the ratio of the oxidizing to reducing species in the adjacent gas phase is larger than its stoichiometric ratio, then a workfunction of said working electrode is reduced, and when oxygen is pumped to said working electrode under conditions such that the ratio of the oxidizing to reducing species in the adjacent gas phase is less than its stoichiometric ratio then the workfunction of said working electrode is increased;
  said working electrode being such that when the oxidizing species are in excess of a stoichiometric amount with respect to the reducing species then the oxidizing species in interaction with said working electrode cause the workfunction to increase, and when the reducing species are in excess of the stoichiometric amount with respect to the oxidizing species then the reducing species in their interaction with said working electrode cause the workfunction to decrease;

said working electrode having an emitting surface and an underlying electrolyte with a dopant species having alkali metal atoms which is thermionically emitted from said working electrode surface as a positive ion into the surrounding gaseous ambient;

said emitting surface, said underlying electrolyte and said dopant species being ones in which the rate of thermionic emission of said dopant species is reversibly increased/decreased with an increase/decrease in the workfunction of said emitting surface;

a collector electrode electrically insulated and spaced from said emitting surface of said working electrode so that a gas phase can establish itself between said collector electrode and said working electrode and emitted ions can be collected at the said collector electrode;

a first circuit means coupled to said emitting surface and said collector electrode to provide a potential difference between said collector electrode and said emitting surface and a current sensing means which has an electrical output proportional to the magnitude of the measured thermionic current;

a second circuit means whose input is coupled to the output of said current sensing means and whose output is coupled to said electrochemical cell so that an electrochemical current of oxygen can be pumped from one side of said electrochemical cell to the other and at a rate depending on the input to said second circuit means from said current sensing means; and a heating element associated with said emitting surface in order to raise the temperature of said emitting surface to a high enough value to allow thermionic emission.

7. An electrochemical sensing structure as recited in claim 6 wherein:

said working electrode and reference are formed of platinum;

said electrolyte is zirconium oxide doped with sufficient yttrium oxide to allow for oxygen ion conductivity; and said electrolyte is shaped like a cylinder closed at one end with said working electrode on an exposed surface and said reference electrode on an interior surface.

* * * * *